United States Patent [19]

Whitesides et al.

[11] Patent Number: 4,480,111
[45] Date of Patent: Oct. 30, 1984

[54] PROCESS FOR THE PREPARATION OF 4-HYDROXY-2,5-DIMETHYL-2,3-DIHYDROFURAN-3-ONE

[75] Inventors: George M. Whitesides, Newton, Mass.; François P. Mazenod, Geneva, Switzerland

[73] Assignee: Firmenich SA, Switzerland

[21] Appl. No.: 467,821

[22] Filed: Feb. 18, 1983

[30] Foreign Application Priority Data

Mar. 26, 1982 [CH] Switzerland .......................... 1869/82

[51] Int. Cl.³ .......................................... C07D 307/60
[52] U.S. Cl. .................................................. 549/477
[58] Field of Search .......................................... 549/477

[56] References Cited

U.S. PATENT DOCUMENTS

| | | | |
|---|---|---|---|
| 3,629,293 | 12/1971 | Peer et al. | 549/477 |
| 3,647,825 | 3/1972 | Shimazaki et al. | 549/477 |
| 3,651,097 | 3/1972 | van den Ouweland et al. | 549/477 |
| 4,181,666 | 1/1980 | Huber et al. | 549/477 |

FOREIGN PATENT DOCUMENTS 1913476 2/1980 Fed. Rep. of Germany .

OTHER PUBLICATIONS

*Japanese Patent Abstracts*, vol. 3, No. 46, (C-43), p. 21, (Apr. 18, 1979).
*Journal of Organic Chemistry*, vol. 45, No. 21, pp. 4139-4143, (1980).
*Chemical Abstracts*, vol. 70, No. 4, p. 254, Abstract No. 11438, (Jan. 27, 1969).
*Chemical Abstracts*, vol. 70, No. 4, p. 254, Abstract No. 11440q, (Jan. 27, 1969).
*Journal of Organic Chemistry*, vol. 38, No. 1, pp. 123-125, (1973).

*Primary Examiner*—Richard L. Raymond
*Attorney, Agent, or Firm*—Pennie & Edmonds

[57] ABSTRACT

4-Hydroxy-2,5-dimethyl-2,3-dihydrofuran-3-one, which is better known by its name "FURANEOL®", is prepared by hydrogenolysis of an alkali- or alkaline earth metal derivative of fructose-1,6-diphosphate or fructose-1- or fructose-6-monophosphate in the presence of a metal catalyst.

9 Claims, No Drawings

PROCESS FOR THE PREPARATION OF 4-HYDROXY-2,5-DIMETHYL-2,3-DIHYDROFURAN-3-ONE

BRIEF SUMMARY OF THE INVENTION

The instant invention provides a process for the preparation of 4-hydroxy-2,5-dimethyl-2,3-dihydrofuran-3-one, which is better known by its tradename "FURANEOL ®" (registered trademark of Firmenich SA, Geneva, Switzerland). The process consists in the hydrogenolysis in a basic medium of an alkali- or alkaline earth metal derivative of fructose-1,6-diphosphate or fructose-1- or fructose-6-monophosphate, or one of their precursors, in the presence of a metal catalyst.

BACKGROUND OF THE INVENTION

FURANEOL ®, the current tradename for 4-hydroxy-2,5-dimethyl-2,3-dihydrofuran-3-one is a valuable flavor ingredient, namely for the reconstitution of meat aroma and fruity flavor compositions, especially strawberry and grapefruit.

Numerous processes for its preparation have been proposed in the past. Among them, a specific mention should be made to those described by L. Re et al. [Helv. Chim. Acta, 56, 1882 (1973)], G. Büchi and E. Demole [J. Org. Chem. 38, 123 (1973)], M. Matsui et al. [Chem. Abstr., 91, 20809q (1979)], V. Huber and H. J. Wild [European Pat. Appln No. 907] and, more recently, C. H. Ross et al. [European Pat. Appln No. 36,433].

The present invention discloses a novel synthetic approach to the industrial preparation of FURANEOL ®.

PREFERRED EMBODIMENTS OF THE INVENTION

According to a preferred embodiment of the invention, suitable fructose-1,6-diphosphate derivatives include for example the trisodium salt of D-fructose-1,6-diphosphate (F-1,6-P$_2$Na$_3$) or the dicalcium salt of D-fructose-1,6-diphosphate (F-1,6-P$_2$Ca$_2$).

Among the active fructose-monophosphate derivatives, barium D-fructose-1-monophosphate (F-1-PBa) and sodium D-fructose-6-monophosphate (F-6-PNa$_2$) are preferred.

Typically, the hydrogenolysis occurs at a pressure higher than the atmospheric pressure and the best yields of the desired end-products have been observed at pressures of from about $1.0 \times 10^5$ to $4.0 \times 10^5$ Pa (equivalent to 15-60 psi).

According to the process of the invention, the hydrogenolysis is carried out in a basic medium, preferably in the presence of an alkali metal hydroxide, e.g. sodium or potassium hydroxide, or a nitrogen organic base, for instance piperidine in a buffer medium. According to a preferred mode of execution, the hydrogenolysis is effected in the presence of piperidine acetate or KOH, this latter reagent being used in an excess of one equivalent based on the starting fructose-phosphate utilized.

As specified above, the hydrogenolysis is promoted by a metal catalyst. To this effect, platinum or, preferably, palladium on charcoal are conveniently employed.

With regard to the reaction temperature, a preferred range of values is of between about 60° and 120° C., preferably however it is of about 90° C. At temperatures higher than the above given upper limit, it becomes often difficult to suppress the formation of by-products originating from the decomposition of the FURANEOL ® already formed.

The reaction is carried out in a protic solvent, in water for instance or in a mixture of water with methanol.

The specific reaction conditions shall be given in the following examples wherein the temperatures are indicated in degrees centigrade.

EXAMPLES

The hydrogenolysis is carried out in a glass vessel equipped with a mechanical stirrer. Reagents are introduced in the following order: fructose-phosphate, solvent (or mixture of solvents), potassium hydroxide or, in certain cases, piperidine acetate and finally the catalyst. The catalyst can be used in association with a cocatalyst such as for example sodium iodide.

Before any introduction of hydrogen, a thorough degazing with argon was systematically carried out. During hydrogenolysis, a pressure of $1-4 \times 10^5$ Pa was maintained in the reaction vessel. Under the said conditions, the reaction was generally completed in 24 hours, the presence of FURANEOL ® being detectable by the appearance of a yellowish color.

After filtration, the clear filtrate was extracted with at least 4 fractions of methylene chloride and the organic phase was separated after addition of a saturated sodium chloride aqueous solution. After the usual treatments of drying over magnesium sulfate and evaporating at reduced pressure, FURANEOL ® was isolated as a yellow solid residue of m.p. 77°-9°. In some instances, it was isolated as a yellowish liquid which crystallizes by cooling at 4° under argon. Analytical samples were obtained by sublimation at 80° and 9.3 Pa. The analytical characteristics were in all respects identical to those of a sample prepared in accordance with a prior known process.

Hydrogenolysis of the calcium salt of D-fructose-1,6-diphosphate

10 G of F-1,6-P$_2$Ca$_2$ of 75% purity (18 mmole) were mixed with 1.34 g of sodium iodide (8.9 mmole) in 50 ml of methanol and 50 ml of water. To this mixture, 1.76 g (31.3 mmole) of KOH were introduced, followed by 200 mg of 10% palladium on charcoal. After having degazed the solution and the reaction vessel with a stream of argon, hydrogen was introduced so that to obtain an internal pressure of about $4 \times 10^5$ Pa. The reaction mixture was then kept at 94° for 24 h, whereupon the metal catalyst and the insoluble inorganic phosphate formed were filtered and the yellowish clear solution was extracted.

After the usual treatments of drying and evaporation, FURANEOL ® was obtained as a yellow oil (660 mg; yield: 28.7%) which crystallized by standing overnight at 4°. Its melting point was 77°-79°.

By carrying out the reaction in a buffer medium and at a lower pressure, 102 mg (1.2 mmole) of piperidine, 3 ml of methanol, 162 mg of glacial acetic acid (2.7 mmole), 3 ml of water, 850 mg (2.09 mmole) of F-1,6-P$_2$Na$_3$ and 10 mg of 10% palladium on charcoal were mixed in the hydrogenolysis vessel. After degazing with argon, an internal pressure of $1 \times 10^5$ Pa was set by the introduction of hydrogen and the mixture was maintained at 96° for 27 h. Crude FURANEOL ® (110 mg; yield: 41%) was obtained by the usual treatments of the obtained mixture.

Hydrogenolysis of F-1-PBa

F-1-PBa trihydrate (500 mg; 1.25 mmole) was subjected to hydrogenolysis as described above by using piperidine acetate and sodium iodide (32 moles %) in a 1:1 (v:v) mixture of water and methanol. After having been kept for 23 h at 92° under a pressure of hydrogen of about $1 \times 10^5$ Pa, the reaction mixture was filtered and worked up as indicated above.

After extraction with methylene chloride followed by drying and evaporation, 20 mg (yield: 14.1%) of crude FURANEOL® were obtained.

Hydrogenolysis of F-6-PNa$_2$ 635 mg of F-6-PNa$_2$ (2.09 mmole; purity 97%) were subjected to hydrogenolysis in a buffer medium in 10 ml of a 1:1 mixture of water/methanol as indicated above. After 24 h at 96° under a pressure of hydrogen of about $1 \times 10^5$ Pa, the mixture was worked up as indicated above. 55 Mg of FURANEOL® (yield 20%) were thus isolated.

Phosphoric acid salts of D-fructose, used as starting materials in the process described above, are commercially available product (origin: Sigma Chem. Co.). The results achieved during several runs are resumed in the following table.

TABLE

| | Starting materials | H$_2$ pressure | solvent | temp. [°C.] | reaction time [h] | reagent [eq.] | NaI [mole %] | yield [%] |
|---|---|---|---|---|---|---|---|---|
| 1. | F—1,6-P$_2$Na$_3$ | 60 | MeOH:H$_2$O | 92 | 24 | 1,6 KOH | 40 | 20 |
| 2. | " | 15 | " | 96 | 27 | Piperidine Ac* | — | 35 |
| 3. | F—1,6-P$_2$Ca$_2$ | 60 | " | 85 | 21 | 1,1 KOH | — | 13 |
| 4. | " | 60 | " | 96 | 24 | 1,7 KOH | — | 33 |
| 5. | " | 60 | " | 95 | 26 | 2 KOH | — | 10 |
| 6. | " | 60 | " | 94 | 24 | 1,7 KOH | 49 | 22 |
| 7. | " | 60 | " | 150 | 6,5 | " | 49 | 25 |
| 8. | " | 60 | H$_2$O | 96 | 23 | " | 49 | 24 |
| 9. | " | 15 | MeOH:H$_2$O | 92 | 21 | Piperidine Ac* | — | 12 |
| 10. | F—1-PBa | 15 | " | 92 | 23 | " | 32 | 10 |
| 11. | F—6-PNa$_3$ | 15 | " | 96 | 24 | " | — | 20 |
| 12. | " | 40 | " | 80 | 16 | KOH | 23 | 11 |

*Piperidine Ac = Piperidine acetate

What we claim is:

1. A process for the preparation of 4-hydroxy-2,5-dimethyl-2,3-dihydrofuran-3-one, which comprises subjecting an alkali- or an alkaline earth metal derivative of fructose-1,6-diphosphate or fructose-1- or fructose-6-monophosphate, or one of their precursors, to hydrogenolysis in a basic medium in the presence of a metal catalyst.

2. A process according to claim 1 wherein the hydrogenolysis is carried out in the presence of KOH.

3. A process according to claim 2 wherein KOH is used in a proportion of about 1.5 to 2 equivalents per equivalent of starting fructose-1,6-diphosphate or fructose-1- or fructose-6-monophosphate.

4. A process according to claim 1 wherein the hydrogenolysis is carried out in the presence of piperidine acetate.

5. A process according to claim 1 wherein the hydrogenolysis is carried out at a pressure of between about 1.0 and $4.0 \times 10^5$ Pa.

6. A process according to claim 1 wherein the hydrogenolysis is effected at a temperature of between 60° and 120° C.

7. A process according to claim 1 wherein the metal catalyst is palladium on charcoal.

8. A process according to claim 1 wherein the hydrogenolysis is carried out in a protic solvent consisting of water or a mixture of water and methanol.

9. A process according to claim 1 wherein the hydrogenolysis is effected at a temperature of up to about 120° C.

* * * * *